United States Patent
Klee et al.

(10) Patent No.: US 10,188,587 B2
(45) Date of Patent: Jan. 29, 2019

(54) DENTAL COMPOSITION

(71) Applicant: DENTSPLY DETREY GMBH, Constance (DE)

(72) Inventors: Joachim E. Klee, Radolfzell (DE); Maximilian Maier, Düsseldorf (DE); Christian Scheufler, Engen (DE)

(73) Assignee: DENTSPLY SIRONA Inc., York, PA (US)

( * ) Notice: Subject to any disclaimer, the term of this patent is extended or adjusted under 35 U.S.C. 154(b) by 33 days.

(21) Appl. No.: 15/034,660

(22) PCT Filed: Dec. 4, 2014

(86) PCT No.: PCT/EP2014/076633
§ 371 (c)(1),
(2) Date: May 5, 2016

(87) PCT Pub. No.: WO2015/082642
PCT Pub. Date: Jun. 11, 2015

(65) Prior Publication Data
US 2016/0256363 A1    Sep. 8, 2016

(30) Foreign Application Priority Data
Dec. 6, 2013  (EP) ..................................... 13005703

(51) Int. Cl.
*A61K 6/083* (2006.01)
*C07D 407/12* (2006.01)

(52) U.S. Cl.
CPC ............ *A61K 6/083* (2013.01); *C07D 407/12* (2013.01)

(58) Field of Classification Search
CPC ............................... A61K 6/083; C07D 407/12
See application file for complete search history.

(56) References Cited

U.S. PATENT DOCUMENTS

| | | | |
|---|---|---|---|
| 6,353,061 B1 * | 3/2002 | Klee ................. | A61K 6/083 433/228.1 |
| 2002/0061995 A1 * | 5/2002 | Ohkuma .............. | C07D 339/06 526/286 |

(Continued)

*Primary Examiner* — Michael F Pepitone
*Assistant Examiner* — Jessica M Roswell
(74) *Attorney, Agent, or Firm* — Dentsply Sirona Inc.

(57) ABSTRACT

Dental composite comprising
(i) a polymerizable composition obtainable by reacting a mixture comprising:

(a) x equivalents of one or more compounds of the following formula (I):

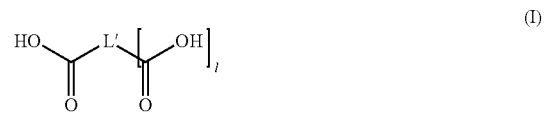

(I)

wherein

L' is an (l+1)-valent hydrocarbon group which may contain in its backbone 1 to 3 heteroatoms selected from oxygen atoms and sulfur atoms and which may be substituted by one or more hydroxyl groups or groups —COOL" wherein L" is a polymerizable moiety;

l is an integer of from 1 to 3;

(b) y equivalents of one or more compounds of the following formula (IIa), (IIb) and/or (IIc):

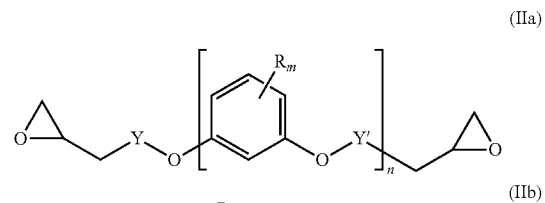

(IIa)

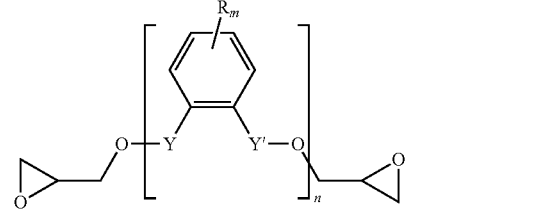

(IIb)

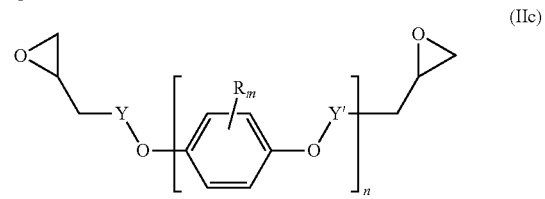

(IIc)

wherein n is an integer of from 1 to 3,

Y may be present or absent, and when present represents a carbonyl group;

Y' independently may be present or absent, represents a carbonyl group;

$R_m$ which may be the same or different represent 1 to 3 substituents selected from halogen atoms, alkyl groups, and alkoxy groups, or wherein two $R_m$ form together with the carbon atoms of the ring to which they are bonded an annelated aromatic ring; and (c) z equivalents of one or more compounds of the following formula (III):

(Continued)

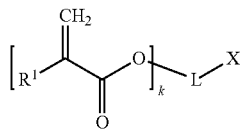

(III)

wherein
R¹ is a hydrogen atom or an alkyl group;
k is an integer of from 1 to 3, whereby
when k is 1, 2 or 3, then L is a (k+1)-valent hydrocarbon group which may contain 1 to 3 heteroatoms selected from oxygen atoms and sulfur atoms, and X is a carboxylic acid group, or a hydroxyl group bonded to an aromatic ring forming part of L; or
wherein $0.05 \leq x/y \leq 0.66$, and $2y-\bar{f}x \leq z \leq 1.5(2y-\bar{f}x)$,
wherein x, y, and z are the molar equivalents of components (a), (b) and (c) and $\bar{f}$ is the mean acid functionality of component (a):

$$\bar{f} = \sum_{l=1}^{3} \frac{x_l}{x}(l+1)$$

wherein l is as defined in formula (I); and
optionally reacting the hydroxyl groups and/or carboxylic acid groups on L' of the reaction product of the mixture with a compound having a polymerizable double bond; and
(ii) a particulate filler.

15 Claims, No Drawings

(56) References Cited

U.S. PATENT DOCUMENTS

2005/0043490 A1* 2/2005 Klee .................... A61K 6/0017
  525/285
2007/0078198 A1* 4/2007 Otsuji .................... C07C 69/54
  523/120

* cited by examiner

DENTAL COMPOSITION

FIELD OF THE INVENTION

The present invention relates to a dental composite. The present invention also relates to a process for the preparation of a composition for use in a dental composite. Furthermore, the present invention relates to a polymerizable composition obtainable by the process of the invention. Finally, the present invention relates to the use of specific polymerizable macromers obtainable by the process of the invention in a dental composite.

A dental composite of the present invention may be a flowable dental composite, a universal dental composite, a packable dental composite or a pit and fissure sealer. A dental composite according to the present invention does not require the use of 2,2-bis[4-(2-hydroxy-3-methacryloyloxy propoxy) phenyl]propane (bis-GMA), bisphenol-A dimethacrylate, ethoxylated bis-GMA, or any other raw material based on bisphenol-A for providing superior properties including mechanical properties, refractive index, and viscosity even in the absence of solvents.

BACKGROUND OF THE INVENTION

Dental composites are known. Conventional dental composites comprise polymerizable monomers and particulate filler. In view of reducing the polymerization shrinkage, conventional dental composites contain bis-GMA and a high filler content. However, bisphenol-A contained in bis-GMA and other polymerizable resins is problematic when leached from the polymerized dental composite. Bisphenol-A is an endocrine disruptor which may have adverse effects on the patient and the dentist alike. Therefore, the use of any bisphenol-A containing polymerizable resin such as bis-GMA in a dental composite is not preferred.

Klee, J. E. et al. Acta Polymer., 44, 163-167 (1993) discloses the synthesis of alpha, omega-methacrylolyl poly (epoxide-carboxylic acid) macromers wherein the epoxide is derived from 2,2-[bis-4(2,3-epoxypropoxy)phenyl]propane.

SUMMARY OF THE INVENTION

It is the problem of the present invention to provide a dental composite which does not require the use of 2,2-bis [4-(2-hydroxy-3-methacryloyloxy propoxy) phenyl]propane (bis-GMA), bisphenol-A dimethacrylate, ethoxylated bis-GMA, or any other raw material based on bisphenol-A for providing superior properties including mechanical properties, refractive index, and viscosity even in the absence of solvents.

It is a further problem of the present invention to provide a process for the preparation of a polymerizable composition which may be used in a dental composite whereby the composition provides superior properties including mechanical properties, refractive index, and viscosity even in the absence of solvents and which does not require the use of 2,2-bis[4-(2-hydroxy-3-methacryloyloxy propoxy) phenyl]propane (bis-GMA), bisphenol-A dimethacrylate, ethoxylated bis-GMA, or any other raw material based on bisphenol-A.

Furthermore, it is the problem of the present invention to provide a polymerizable composition which may be used for the preparation of a dental composite and which does not require the use of 2,2-bis[4-(2-hydroxy-3-methacryloyloxy propoxy) phenyl]propane (bis-GMA), bisphenol-A dimethacrylate, ethoxylated bis-GMA, or any other raw material based on bisphenol-A for providing superior properties including mechanical properties, refractive index, and viscosity even in the absence of solvents.

Furthermore, it is the problem of the present invention to provide specific polymerizable macromers for use in a dental composite.

According to a first aspect, the present invention provides a dental composite comprising
(i) a polymerizable composition obtainable by reacting a mixture comprising:
  (a) x equivalents of one or more compounds of the following formula (I):

wherein
L' is an (l+1)-valent hydrocarbon group which may contain in its backbone 1 to 3 heteroatoms selected from oxygen atoms and sulfur atoms and which may be substituted by one or more hydroxyl groups or groups —COOL" wherein L" is a polymerizable moiety;
l is an integer of from 1 to 3;
  (b) y equivalents of one or more compounds of the following formula (IIa), (IIb) and/or (IIc):

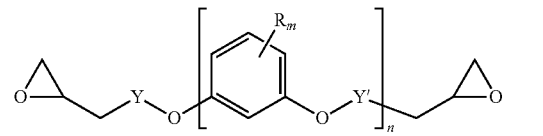

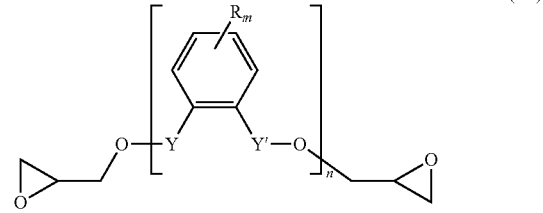

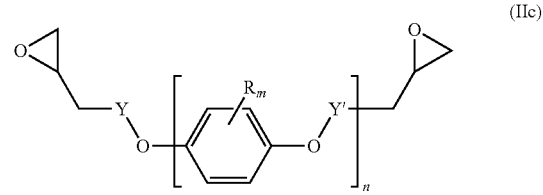

wherein
n is an integer of from 1 to 3,
Y may be present or absent, and when present represents a carbonyl group;
Y' independently may be present or absent, represents a carbonyl group;
$R_m$ which may be the same or different represent 1 to 3 substituents selected from halogen atoms, alkyl groups, and alkoxy groups, or wherein two IR, form together with the carbon atoms of the ring to which they are bonded an annelated aromatic ring; and (c) z equivalents of one or more compounds of the following formula (III):

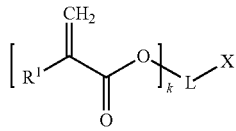

wherein
R¹ is a hydrogen atom or an alkyl group;
k is an integer of from 1 to 3, whereby
when k is 1, 2 or 3, then L is a (k+1)-valent hydrocarbon group which may contain 1 to 3 heteroatoms selected from oxygen atoms and sulfur atoms, and X is a carboxylic acid group, or a hydroxyl group bonded to an aromatic ring forming part of L; or
when k is 1, L represents a single bond and X is a hydrogen atom,
wherein $0.05 \leq x/y \leq 0.66$, and $2y - \bar{f}x \leq z \leq 1.5(2y - \bar{f}x)$,
wherein x, y, and z are the molar equivalents of components (a), (b) and (c) and $\bar{f}$ is the mean acid functionality of component (a):

$$\bar{f} = \sum_{l=1}^{3} \frac{x_l}{x}(l+1)$$

wherein l is as defined in formula (I),
and optionally reacting the hydroxyl groups on L' of the reaction product of the mixture with a compound having a polymerizable double bond; and
(ii) a particulate filler.

According to a second aspect, the present invention provides process for the preparation of a dental composition, which comprises reacting a mixture comprising:
a) x equivalents of one or more compounds of the following formula (I):

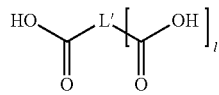 (I)

wherein
L' is an (l+1)-valent hydrocarbon group which may contain in its backbone 1 to 3 heteroatoms selected from oxygen atoms and sulfur atoms and which may be substituted by one or more hydroxyl groups or groups —COOL" wherein L" is a polymerizable moiety;
l is an integer of from 1 to 3;
(b) y equivalents of one or more compounds of the following formula (IIa), (IIb) and/or (IIc):

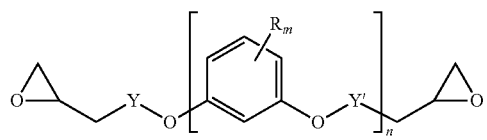 (IIa)

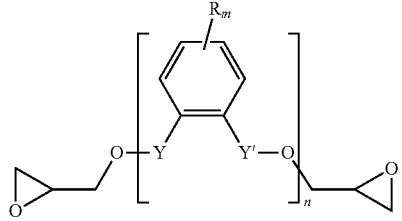 (IIb)

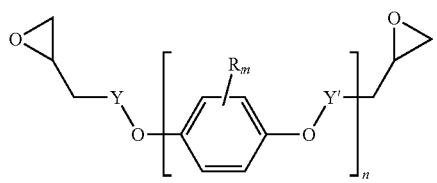 (IIc)

wherein
n is an integer of from 1 to 3,
Y may be present or absent, and when present represents a carbonyl group;
Y' independently may be present or absent, represents a carbonyl group;
$R_m$ which may be the same or different represent 1 to 3 substituents selected from halogen atoms, alkyl groups, and alkoxy groups, or wherein two $R_m$ form together with the carbon atoms of the ring to which they are bonded an annelated aromatic ring; and
(c) z equivalents of one or more compounds of the following formula (II):

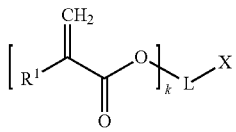 (III)

wherein
R¹ is a hydrogen atom or an alkyl group;
k is an integer of from 1 to 3, whereby
when k is 1, 2 or 3, then L is a (k+1)-valent hydrocarbon group which may contain 1 to 3 heteroatoms selected from oxygen atoms and sulfur atoms, and X is a carboxylic acid group, or a hydroxyl group bonded to an aromatic ring forming part of L; or
when k is 1, L represents a single bond and X is a hydrogen atom,
wherein $0.05 \leq x/y \leq 0.66$, and $2y - \bar{f}x \leq z \leq 1.5(2y - \bar{f}x)$,
wherein x, y, and z are the molar equivalents of components (a), (b) and (c) and $\bar{f}$ is the mean acid functionality of component (a):

$$\bar{f} = \sum_{l=1}^{3} \frac{x_l}{x}(l+1)$$

wherein l is as defined in formula (I),
and optionally reacting the hydroxyl groups on L' of the reaction product of the mixture with a compound having a polymerizable double bond.

According to a third aspect, the present invention provides a polymerizable composition obtainable by the process of the invention. The dental composite contains specific macromers.

According to a fourth aspect, the present invention provides the use of the specific polymerizable macromers in a dental composite.

The present invention is based on the recognition that polymerizable macromers contained in a polymerizable composition of the invention may replace bis-GMA or any other polymerizable resin containing bisphenol-A in a dental composite. The polymerizable macromers provide superior properties including mechanical properties, refractive index, and viscosity even in the absence of solvents.

DETAILED DESCRIPTION OF THE PREFERRED EMBODIMENTS

The present invention provides a dental composite. A dental composite of the present invention may be a flowable dental composite, a universal dental composite, packable dental composite or a pit and fissure sealer. Preferably, the dental composite of the present invention is a universal dental composite or a packable dental composite.

The dental composite of the present invention comprises a polymerizable composition and a particulate filler.

The polymerizable composition is obtainable by reacting a mixture comprising one or more polycarboxylic acids (a), one or more diepoxide compounds (b) and one or more chain terminating compounds (c). Accordingly, component (a) contains one or more compounds of formula (I). Component (b) contains one or more compounds of one of the formulae (IIa), (IIb), and (IIc). Component (c) contains one or more compounds of formula (IIII).

The mixture contains x molar equivalents of component (a), y molar equivalents of component (a), and z molar equivalents of component (c).

The molar equivalents are adjusted so that $0.05 \leq x/y \leq 0.66$, and $2y-\bar{f}x \leq z \leq 1.5(2y-\bar{f}x)$, wherein $\bar{f}$ is the mean acid functionality of component (a) defined by the following formula:

$$\bar{f} = \sum_{l=1}^{3} \frac{x_l}{x}(l+1)$$

wherein l is as defined in formula (I) and $x_l/x$ is the molar fraction of the compounds having an acid functionality of l+1.

Accordingly, the molar equivalents x of component (a) depends on the functionality of the one or more polycarboxylic acids contained in component (a). According to a preferred embodiment, l is 1. When l is 1, then $\bar{f}$ is 2. According to a further preferred embodiment, the mixture contains one compound of formula (I), preferably wherein l is 1.

According to the present invention, the molar equivalent y is larger than the molar equivalent x in that $0.05 \leq x/y \leq 0.66$. Given that y>x and depending on the mol ratio of r'=x/y, the polymerization degree ($P_a$) increases according to $P_a=(1+r')/(1-r')$. In case x/y>0.66, the viscosity of the polymerizable composition may become excessively large so that large amounts of a solvent or reactive diluent are required for providing a dental composite of the present invention. In case x/y<0.05, the polymerizable composition contains an excess of reaction products between component (b) and component (c) whereby the mechanical properties of the dental composite of the present invention are deteriorated.

The mixture contains z molar equivalents of a one or more and chain terminating compounds (c). The amount of z is selected according to the present invention so that $2y-\bar{f}x \leq z \leq 1.5(2y-\bar{f}x)$, wherein $\bar{f}$ is the mean acid functionality of component (a) defined above. Preferably, z is $2y-\bar{f}x$. In case $x<2y-\bar{f}x$, then the content of polymerizable end groups in the macromers contained in the polymerizable composition of the present invention may be reduced which is not preferable in view of the mechanical properties of the dental composite of the present invention. In case $z>1.5(2y-\bar{f}x)$, the excess of chain terminating monomer may compete with the reaction of component (a) and component (b) and interfere with the macromer formation.

The average molecular weight $\bar{M}$ of the polymerizable composition may be estimated according to the following formula:

$$\bar{M}=x\bar{M_{(a)}}+y\bar{M_{(b)}}+z\bar{M_{(c)}}$$

In the above formula $\bar{M_{(a)}}$ is the average molecular weight of component (a), $\bar{M_{(b)}}$ is the average molecular weight of component (b), and $\bar{M_{(c)}}$ is the average molecular weight of component (c).

A polycarboxylic acid (a) is a compound of the following formula (I):

In formula (I), L' is an (l+1)-valent hydrocarbon group which may contain in its backbone 1 to 3 heteroatoms selected from oxygen atoms and sulfur atoms and which may be substituted by one or more hydroxyl groups or groups —COOL" wherein L" is a polymerizable moiety.

Preferably, L' is a divalent hydrocarbon group which may contain in its backbone 1 to 3 heteroatoms oxygen atoms. Preferably, L' may be substituted by one or more hydroxyl groups or groups —COOL" wherein L" is a polymerizable moiety. The group —COOL" polymerizable may be a hydroxyalkyl methacrylate ester.

An (l+1)-valent hydrocarbon group may be derived from a an aliphatic, alicyclic or aromatic hydrocarbon group. Preferably, the (l+1)-valent hydrocarbon group is an aliphatic (l+1)-valent hydrocarbon group.

l is an integer of from 1 to 3. Preferably, l is 1, whereby a compound of formula (I) is a dicarboxylic acid according to the following formula (Ia):

In formula (Ia), L' may be a divalent aliphatic group or an aromatic group. The aliphatic group may be a straight chain, branched or cyclic group which may contain 1 to 20 carbon atoms, preferably 2 to 8 carbon atoms.

Specific examples of the aliphatic group L' are a methylene group, an ethylene, a 1,2-propylene group, a 1,3-propylene group, a 1,4-butylene group, and a 1,6-hexylene group.

The aromatic group may be an aromatic group containing 6 to 10 carbon atoms, preferably 6 carbon atoms.

Specific examples of the aromatic group L' are 1,2-phenylene 1,3-phenylene, 1,4-phenylene.

Examples of the aliphatic dicarboxylic acids (a) include linear, branched or cyclic aliphatic dicarboxylic acids such maleic acid, itaconic acid, fumaric acid, adipic acid, glutaric acid, succinic acid, and cyclohexanedicarboxylic acid including 1,4-cyclohexanedicarboxylic acid and 1,3-cyclohexanedicarboxylic acid.

Specific examples of the aromatic dicarboxylic acid (a) are phthalic acid, terephthalic acid, isophthalic acid, 2,6-naphthalenedicarboxylic acid, and diphenyldicarboxylic acid.

According to a preferred embodiment, the polymerizable composition is obtainable by reacting the hydroxyl groups on L' of the reaction product of the mixture with a compound having a polymerizable double bond.

A diepoxide (b) is a compound of the following formula (IIa), (IIb) and/or (IIc):

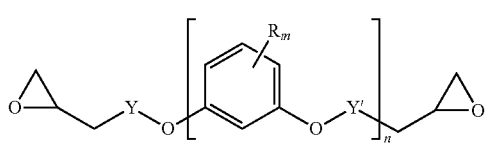

(IIa)

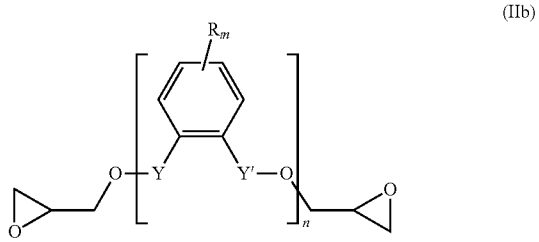

(IIb)

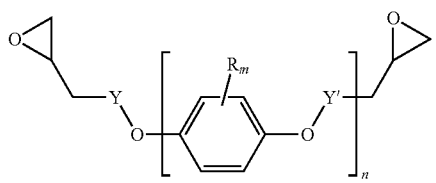

(IIc)

Preferably, the diepoxide (b) is a compound of formula (IIa) or (IIb). Most preferably, the main component of the diepoxide (b) is a compound of formula (IIa).

In the formula (IIa), (IIb) and/or (IIc), n is an integer of from 1 to 3. Preferably, n is 1. Y may be present or absent, and when present represents a carbonyl group.

Y' independently may be present or absent, represents a carbonyl group.

$R_m$ which may be the same or different represent 1 to 3 substituents selected from halogen atoms, alkyl groups, and alkoxy groups, or wherein two $R_m$ form together with the carbon atoms of the ring to which they are bonded an annelated aromatic ring.

Specific examples of the diepoxide (b) are terephtalic acid diglycidyl ester, 1,2-diglycidyl phtalate, resorcinol diglycidyl ether, catechol diglycidyl ether, and hydroquinone diglycidyl ether.

A chain terminating compound (c) is a compound of the following formula (III):

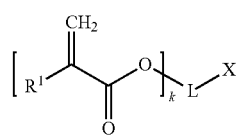

(III)

In formula (III), $R^1$ is a hydrogen atom or an alkyl group.

Moreover, in formula (III), k is an integer of from 1 to 3. Preferably, k is 1.

When k is 1, 2 or 3, then L is a (k+1)-valent hydrocarbon group which may contain 1 to 3 heteroatoms selected from oxygen atoms and sulfur atoms, and X is a carboxylic acid group, or a hydroxyl group bonded to an aromatic ring forming part of L. An (k+1)-valent hydrocarbon group may be derived from a an aliphatic, alicyclic or aromatic hydrocarbon group. Preferably, the (k+1)-valent hydrocarbon group is an aromatic (k+1)-valent hydrocarbon group.

Alternatively, when k is 1, L represents a single bond and X is a hydrogen atom, According to a preferred embodiment, k is 1, L represents a single bond and X is a hydrogen atom.

Specific examples of the chain terminating compound (c) are acrylic acid and methacrylic acid, Optionally, the hydroxyl groups on L' of the reaction product of the mixture may be reacted with a compound having a polymerizable double bond. The compound having a polymerizable double bond may be a hydroxyalkyl (meth)acrylate. Examples of suitable compounds are 2-hydroxyethyl methacrylate (HEMA).

The polymerizable composition obtainable by reacting polycarboxylic acids (a), diepoxide compounds (b) and chain terminating compounds (c) contains polymerizable macromers of one of the following formulae (IVa), (IVb), and/or (IVc):

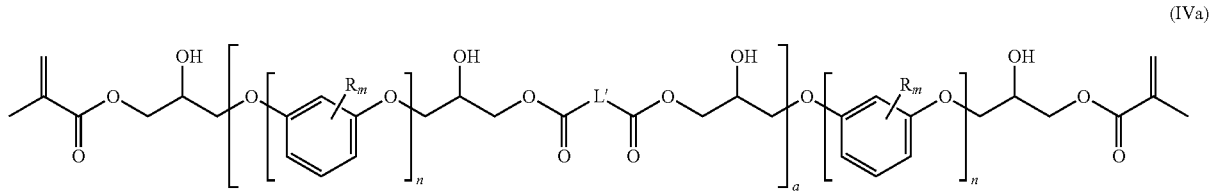

(IVa)

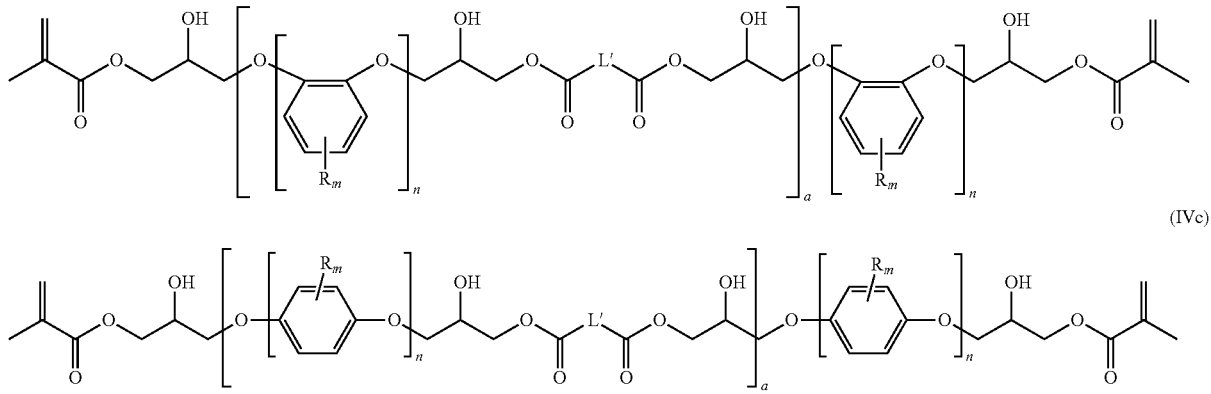

wherein $R^1$, $R_m$, n, and L' are as defined above,

The average chain length a is in the range of from 0.05 to 1.5.

The dental composite of the present invention comprises a particulate filler. A particulate filler is a powdered metal oxide or hydroxide, mineral silicate, or ion leachable glass or ceramic. Examples of particulate fillers may be selected from fillers currently used in dental restorative compositions.

The particulate filler may have a unimodal or polymodal (e.g., bimodal) particle size distribution. The particulate filler can be an inorganic material. It can also be a cross-linked organic material that is insoluble in the polymerizable resin, and is optionally filled with inorganic filler. The particulate filler can be radiopaque, radiolucent or non-radiopaque.

Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and sub-micron silica particles such as pyrogenic silicas. Examples of suitable particulate organic filler particles include filled or unfilled pulverized polycarbonates or polyepoxides.

Preferably the surface of the filler particles is treated with a coupling agent in order to enhance the bond between the particulate filler and the matrix. The use of suitable coupling agents include gamma-methacryloxypropyltrimethoxysilane, gamma-mercaptopropyltriethoxysilane and gamma-aminopropyltrimethoxysilane.

The particulate filler usually has an average particle size of from 0.005 to 100 μm, preferably of from 0.01 to 40 μm as measured using, for example, by electron microscopy or by using a conventional laser diffraction particle sizing method as embodied by a MALVERN Mastersizer S or MALVERN Mastersizer 2000 apparatus.

The dental composite of the present invention may contain nano-scale particles. As the nano-scale particles in the present invention, any known nano-scale particles used in dental compositions may be used without any limitation. Preferable examples of the nano-scale particles include particles of inorganic oxides such as silica, alumina, titania, zirconia, particles of composite oxides of any of these oxides, and particles of calcium phosphate, hydroxyapatite, yttrium fluoride and ytterbium fluoride. Preferably, the nano-scale particles are particles of silica, alumina, titania, prepared by flame pyrolysis.

The average particle size of the nano-scale particles is preferable 1 to 50 nm, and more preferably 3 to 40 nm. The average particle size of the nano-scale particles can be measured by taking electron micrographs of these nano-scale particles and calculating the average value of the diameters of the 100 randomly-selected nano-scale particles. It is desirable that the inorganic nano-scale particles be subjected previously to surface treatment with a surface treating agent to improve the affinity between the inorganic filler and the polymerizable composition of the present invention, and to increase the chemical bonding between the inorganic filler and the polymerizable composition so as to enhance the mechanical strength of the cured product.

The total amount of the particulate filler is preferably 50 to 400 parts by weight per 100 parts by weight of the polymerizable composition, more preferably 75 to 350 parts by weight, and particularly preferably 100 to 300 parts by weight. The amount of the nano-scale particles is preferably 0.1 to 50 parts by weight per 100 parts by weight of the polymerizable composition, more preferably 1 to 40 parts by weight, and particularly preferably 3 to 30 parts by weight.

Preferably, the polymerizable composition (i) contained in the dental composite according to the present invention has a dynamic viscosity at 23° C. of from 1 to 30 Pas.

Moreover, the polymerizable composition (i) contained in the dental composite according to the present invention has a refractive index of from 1.500 to 1.540.

The present invention provides a process for the preparation of a polymerizable composition for use in a dental composite, in particular in the dental composite of the present invention.

The process comprises the reaction of a mixture comprising (a) x equivalents of one or more compounds of the formula (I) as defined above (b) y equivalents of one or more compounds of the formula (IIa), (IIb) and/or (IIc) as defined above, and (c) z equivalents of one or more compounds of the formula (III) as defined above, wherein $0.05 \leq x/y \leq 0.66$, and $2y - \bar{f}x \leq z \leq 1.5(2y - \bar{f}x)$, wherein x, y, and z are the molar equivalents of components (a), (b) and (c) and $\bar{f}$ is the mean acid functionality of component (a):

$$\bar{f} = \sum_{l=1}^{3} \frac{x_l}{x}(l+1)$$

wherein l is as defined in formula (I), and optionally reacting the hydroxyl groups on L' of the reaction product of the mixture with a compound having a polymerizable double bond.

The reaction may be carried out by mixing, preferably during heating, of components (a), (b) and (c) in a reaction vessel and reacting the mixture in a single step for providing a polymerizable composition of the present invention.

Alternatively, the reaction may be carried out by mixing components (a) and (b) for providing a first mixture and reacting the first mixture in a first step, and subsequently adding component (c) the reaction product of the first step for providing a second mixture and then reacting the second mixture for providing a polymerizable composition of the present invention.

The reaction time is not particularly limited and may be selected in the range from 30 minutes to 48 hours. Preferably, the reaction time is selected in the range of from 1 hours to 12 hours, more preferably, from 2 hours to 10 hours.

The reaction temperature is not particularly limited and may be selected in the range from ambient temperature to the boiling temperature of the mixture. Preferably, the reaction temperature is selected in the range of from 50° C. to the 150° C., more preferably from 70° C. to 130° C.

The reaction pressure is not particularly limited and may be selected in the range from ambient pressure to an elevated pressure. Preferably, the reaction pressure is ambient pressure.

The reaction may be carried out in the presence or absence of a solvent. Suitable solvent may be selected from aprotic solvents such as dimethyl sulfoxide, toluene, DMF, and ethyleneglycol monomethyl ether. Preferably, the reaction is carried out in the absence of a solvent.

The reaction may be carried out in the presence of a catalyst. The catalyst may be a phase transfer catalyst. A suitable phase transfer catalyst may be selected from quaternary ammonium and phosphonium salts. Specifically, the phase transfer catalyst may be triethylbenzyl ammonium chloride, benzyltrimethyl ammonium chloride and hexadecyltributylphosphonium bromide. Preferably, triethylbenzyl ammonium chloride may be used.

The amount of the catalyst is not particularly limited and may be selected in a range of from 0.01 to 5 percent by weight, more preferably 0.1 to 3 percent by weight, based on the total weight of components (a), (b), and (c) present in the reaction mixture.

When component (c) is present in the reaction mixture, the reaction may be carried out in the presence of an inhibitor. The inhibitor may be any conventionally known inhibitor which does not interfere with the desired reaction. The inhibitor may be selected from 2,6-di-tert-butyl-p-cresol and butylated hydroxytoluene (BHT) Preferably, 2,6-di-tert-butyl-p-cresol may be used.

The amount of the inhibitor is not particularly limited and may be selected in a range of from 0.001 to 0.5 percent by weight, more preferably 0.01 to 0.3 percent by weight, based on the total weight of components (a), (b), and (c) present in the reaction mixture.

The obtained methacrylate terminated macromer is may be soluble in organic solvents such as chloroform, DMF and THF and in reactive diluents such as triethyleneglycol dimethacrylate.

The present invention further provides a polymerizable composition obtainable by the process of the present invention.

Preferably, the polymerizable composition according to the present invention has a dynamic viscosity at 23° C. of from 1 to 30 Pas.

Preferably, the polymerizable composition according to the present invention has a refractive index of from 1.500 to 1.540.

The polymerizable composition comprises polymerizable macromers of one of the following formulae (IVa), (IVb), and/or (IVc):

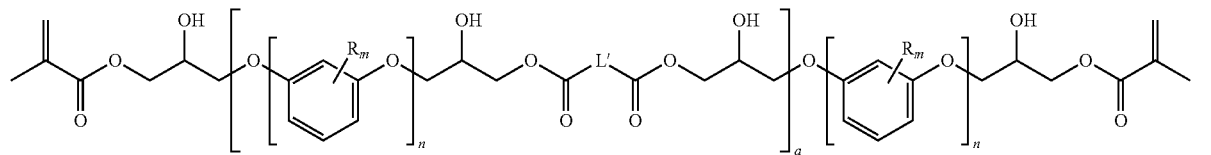

(IVa)

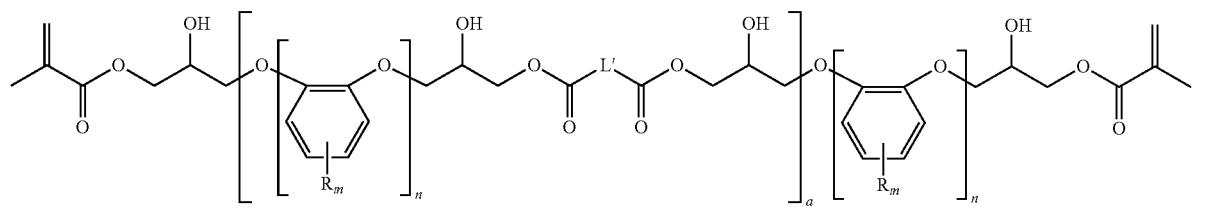

(IVb)

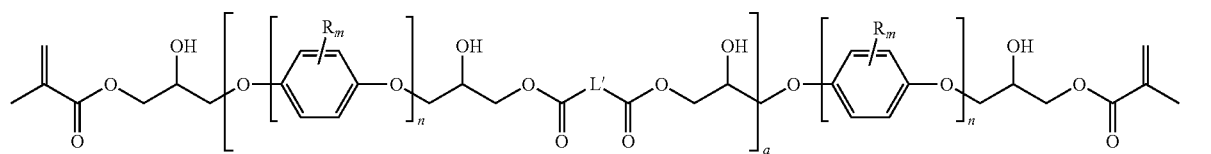

(IVc)

wherein $R^1$, $R_m$, n, and L' are as defined above.

Preferably, "a" is an average chain length which is in the range of from 0.05 to 1.5.

Specific examples of the macromers are as follows:

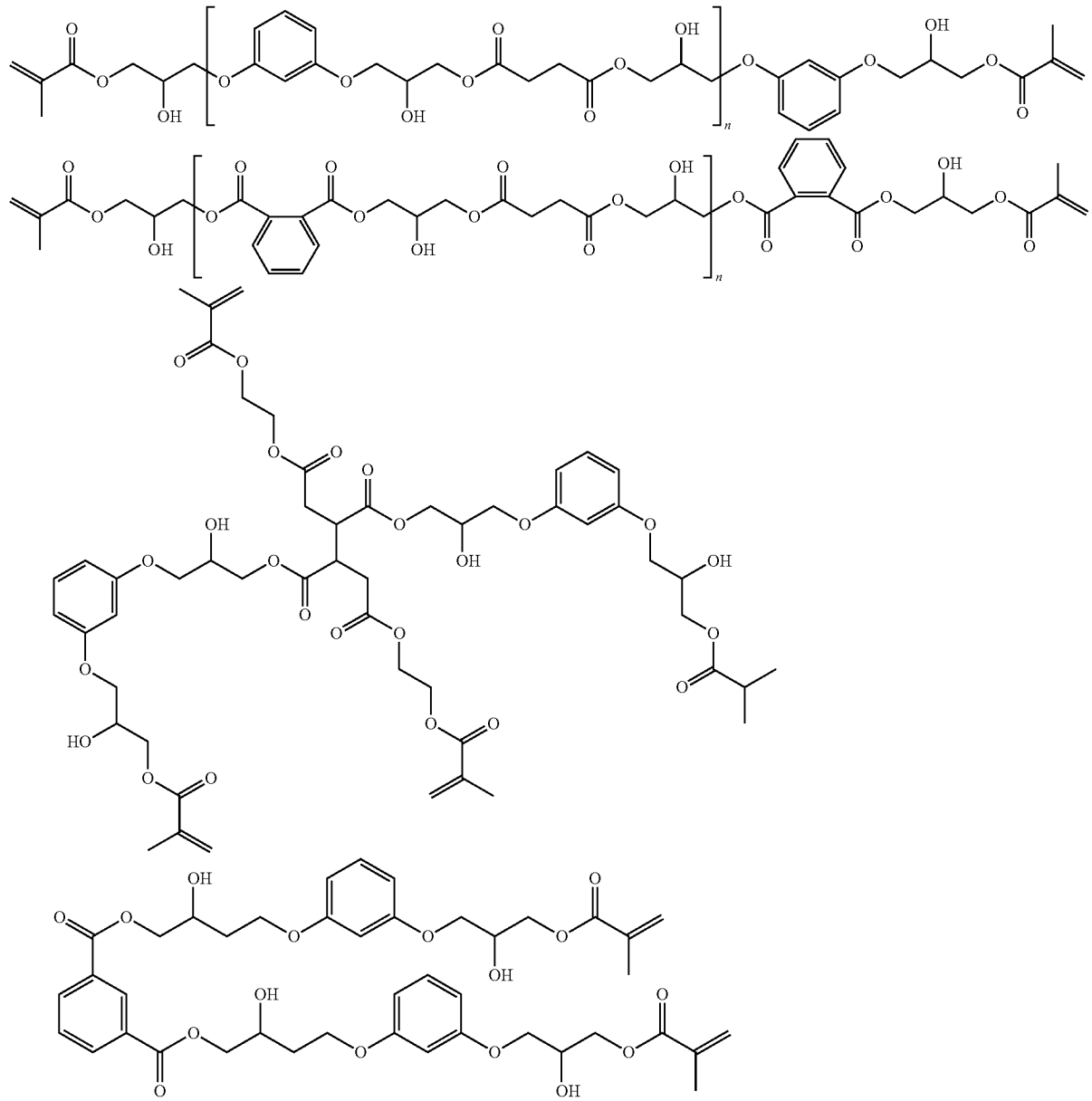

A polymerizable macromer may be used in a dental composite. Preferably, the dental composite is a flowable dental composite, a universal dental composite, packable dental composite or a pit and fissure sealer.

The dental composite of the present invention may contain further polymerizable monomers other than reaction product of components (a), (b), and (c). The polymerizable monomers may be mono-, bi-, tri- or polyfunctional monomers. The polymerizable monomers may be selected from methyl (meth)acrylate, isobutyl (meth)acrylate, benzyl (meth)acrylate, lauryl (meth)acrylate, 2-(N,N-dimethylamino)ethyl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N-(dihydroxyethyl) (meth)acrylamide, (meth)acryloyloxydodecylpyridinium bromide, (meth)acryloyloxydodecylpyridinium chloride, (meth)acryloyloxyhexadeylpyridinium chloride, (meth)acryloyloxydecylammonium chloride, ethylene glycol di(meth)acrylate, triethylene glycol di(meth)acrylate, propylene glycol di(meth)acrylate, neopentyl glycol di(meth)acylate, 1,6-hexanediol di(meth)acrylate, 1,10-decanediol di(meth)acrylate, bisphenol A diglycidyl (meth)acrylate (2,2-bis[4-[3-(meth)acryloyloxy-2-hydroxypropoxy]phenyl]propane, commonly known as "BisGMA"), 2,2-bis[4-(meth)acryloyloxyethoxyphenyl]propane, 2,2-bis[4-(meth)acryloyloxyolyothoxyphenyl]propane, 2,2-bis[4-[3-((meth)acryloyloxy-2-hydroxypropoxy]phenyl]propane, 1,2-bis[3-(meth)acryloyloxy-2-hydroxypropoxylethane, pentaerythritol di(meth)acrylate, [2,2,4-trimethylhexamethylenebis(2-carbamoyloxyethyl)]dimethacrylate (commonly known as "UDMA trimethylolpropane tri(meth)acrylate, trimethylolethane tri(meth)acrylate, tetramethylolmethane tri(meth)acrylate, pentaerythritol tetra(meth)acrylate, dipentaerythritol hexa(meth)acrylate, N,N'-(2,2,4-trimethylhexamethylene)bis[2-(aminocarbonyloxy)propane-1,3-diol]tetramethacrylate, and 1,7-diacryloyloxy-2,2,6,6-tetraacryloyloxymethyl-4-oxyheptane.

The total amount of the polymerizable monomers contained in the dental composite besides the polymerizable composition containing macromers is preferably in the range of from 1 part to 100 part by weight per 100 part by weight of the reaction product of components (a), (b), and (c) of the polymerizable composition.

The dental composite of the present invention preferably contains a polymerization initiator. The type of the polymerization initiator is not particularly limited and can be selected from polymerization initiators commonly used in the dental field. Particularly, photopolymerization initiators and chemical polymerization initiators may b used alone, or two or more of them may be used in combination.

Examples of suitable photopolymerization initiators include alpha-diketones or (bis)acylphosphine oxides.

Examples of the alpha-diketones used as the photopolymerization initiator include camphorquinone, 9,10-phenanthrenequinone, 2,3-pentadione, 2,3-octadione, 4,4'-oxybenzyl, and acenaphthenequinone. Camphorquinone having the maximum absorption wavelength in the visible light range is preferred.

Examples of the acylphosphine oxides include 2,4,6-trimethylbenzoylmethoxyphenylphosphine oxide, 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate.

Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

A chemical polymerization initiator may be an organic peroxide selected from ketone peroxide, hydroperoxide, diacyl peroxide, dialkyl peroxide, peroxyketal, peroxyester, and peroxydicarbonate.

A ketone peroxide may be selected from methyl ethyl ketone peroxide, methyl isobutyl ketone peroxide, methylcyclohexanone peroxide, and cyclohexanone peroxide.

A hydroperoxide may selected from 2,5-dimethylhexane-2,5-dihydroperoxide, diisopropylbenzene hydroperoxide, cumene hydroperoxide, and t-butyl hydroperoxide.

A diacyl peroxide may be selected from acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

A dialkyl peroxide may be selected from di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

A peroxyketal may be selected from 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester.

A peroxyester may be selected form t-butvlperoxy acetate, t-butylperoxy-2-ethyl hexanoate, alpha-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, di-t-butylperoxy isophthalate, di-t-butylperoxy hexahydroterephthalate, t-butylperoxy-3,3,5-trimethyl hexanoate, t-butylperoxy benzoate, and t-butylperoxymaleic acid.

A peroxydicarbonate maybe selected from di-3-methoxy peroxydicarbonate, di-2-ethylhexyl peroxydicarbonate, bis(4-t-butyleyelohexyl)peroxydicarbonate, diisopropyl peroxydicarbonate, di-n-propyl peroxydicarbonate, di-2-ethoxyethyl peroxydicarbonate, and diallyl peroxydicarbonate.

Benzoyl peroxide is preferred.

The amount of the polymerization initiator to be added in the present invention is not particularly limited. Preferably, 0.01 to 10 parts by weight of the polymerization initiator per 100 parts by weight of the polymerizable composition may be used. When the amount of the polymerization initiator is less than 0.01 part by weight, polymerization may not proceed sufficiently and thereby mechanical strength may be reduced. Therefore, the amount is more preferably at least 0.1 part by weight. On the other hand, when the amount of the polymerization initiator exceeds 10 parts by weight, in the case where the polymerization initiator itself has low polymerization performance, sufficient mechanical strength may not be obtained and furthermore precipitation from the composition may occur.

The dental composite of the present invention may further contain a polymerization accelerator. Examples of the polymerization accelerator are amines and sulfinic acids and salts thereof.

Amines may be aliphatic amines or aromatic amines. Examples of aliphatic amines include primary aliphatic amines such as n-butylamine, secondary aliphatic amines such as diisopropylamine, and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine, tertiary aliphatic amines are preferred. Aromatic amines may be selected from N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone.

A sulfinic acid or salt thereof may be selected from sodium benzenesulfinate, sodium p-toluenesulfinate, and sodium 2,4,6-triisopropylbenzenesulfinate.

The amount of polymerization accelerator is not particularly limited. The amount may be selected from the range of from 0.001 to 5 parts by weight of polymerization accelerator per 100 parts by weight of the polymerizable composition.

The dental composite of the present invention may further contain a pH adjuster, an ultraviolet absorber, an antioxidant, a polymerization inhibitor, a colorant, an antibacterial agent, an X-ray contrast agent, a thickening agent, a fluorescent agent.

The dental composite of the present invention may further contain a fluorine ion sustained-releasable filler, such as sodium fluoride, calcium fluoride, fluoroaluminosilicate glass, or sodium monofluorophosphate.

The dental composite may contain an antimicrobial agent. The antimicrobial agent may be a surfactant having an antibacterial activity, such as 12-(meth)acryloyloxydodecylpyridinium bromide or cetylpyridinium chloride.

The present invention will now be further illustrated based on the following examples.

EXAMPLES

Example 1 (AG 18-127-1)

100.000 g (0.450 mol) resorcinol diglycidyl ether, 17.712 g (0.15 mol) succinic acid, 51.650 (0.60 mol) methacrylic acid, 0.847 g triethylbenzyl ammoniumchloride and 0.169 g 2,6-di-tert-butyl-p-cresol were homogeneously mixed during heating to 90° C. and reacted for 6.5 hours at 90° C.

The obtained methacrylate terminated macromer is soluble in organic solvents such as chloroform, DMF and THF and in reactive diluents such as triethylene glycol dimethacrylate.

$M_n$(calc.)=564.59 g/mol $\eta$=41.7±0.4 Pa*s, $n_D^{2D}$=1.5285, $\Delta_R H$=−80.4±0.8 kJ/mol The obtained macromere was dissolved in different reactive diluents as summarized in Table 1:

| Reactive diluent | Unit | SR 9003 [a] | DDDMA [b] | TGDMA [c] |
|---|---|---|---|---|
| concentration | % | 3 | 3 | 30 |
| Viscosity | Pas | 10.3 ± 0.3 | 8.8 ± 2.7 | 4.1 |
| Refractive index | — | 1.5175 | 1.5181 | 1.506 |
| Flexural strength | MPa | 93.2 ± 5.9 | 103.6 ± 3.9 | 91.34 ± 2.59 |
| E-Modulus | MPa | 1919 ± 174 | 2184 ± 63 | 1928 ± 123 |

[a] propoxylated neopentyl glycol diacrylate
[b] 1,12-dodecandiol dimethacrylate
[c] triethylene glycol dimethacrylate

Example 2 (MAM 01-10-02)

15.000 g (0.539 mol) terephtalic acid diglycidyl ester, 1.273 g (0.108 mol) succinic acid, 7.425 (0.315 mol) methacrylic acid, 0.118 g triethylbenzyl ammoniumchloride and 0.024 g 2,6-di-tert-butyl-p-cresol were homogeneously mixed during heating to 90° C. and reacted for 6.5 hours at 90° C.

The obtained methacrylate terminated macromer is soluble in organic solvents such as chloroform, DMF and THF and in reactive diluents such as triethylene glycol dimethacrylate.

$\eta$=256 Pa*s, $n_D^{2D}$=1.520

The obtained macromere was dissolved in TGDMA as summarized in Table 1:

| Batch | | MAM 01-10-02-T30 |
|---|---|---|
| Concentration TGDMA | % | 30 |
| Viscosity | Pas | 1.8 |
| Refractive index | — | 1.499 |
| Flexural strength | MPa | 99.80 ± 3.64 |
| E-Modulus | MPa | 2078 ± 117 |

Example 3 (MAM 01-10-03)

15.000 g (0.539 mol) terephtalic acid diglycidyl ester, 1.403 g (0.108 mol) itaconic acid, 7.425 (0.315 mol) methacrylic acid, 0.118 g triethylbenzyl ammoniumchloride and 0.024 g 2,6-di-tert-butyl-p-cresol were homogeneously mixed during heating to 90° C. and reacted for 6.5 hours at 90° C.

The obtained methacrylate terminated macromer is soluble in organic solvents such as chloroform, DMF and THF and in reactive diluents such as triethylene glycol dimethacrylate.

$\eta$=347 Pa*s, $n_D^{2D}$=1.522

The obtained macromere was dissolved in TGDMA as summarized in Table 1:

| Batch | | MAM 02-10-03-T30 |
|---|---|---|
| concentration | % | 30 |
| Viscosity | Pas | 1.9 |
| Refractive index | — | 1.499 |
| Flexural strength | MPa | 105.8 ± 3.25 |
| E-Modulus | MPa | 2311 ± 181 |

Example 4 (CBI 2-28-2)

5.480 g (0.025 mol) resorcinol diglycidyl ether, 2.048 g (0.012 mol) isophthalic acid, 2.123 g (0.025 mol) methacrylic acid, 0.056 g triethylbenzyl ammoniumchloride and 0.003 g 2,6-di-tert-butyl-p-cresol were homogeneously mixed during heating to 90° C. and reacted for 3 hours at 90° C. Thereafter, to this mixture were added further 2.740 g (0.012 mol) resorcinol diglycidyl ether and 2.123 g (0.025 mol) methacrylic acid and reacted for 3 hours at 90° C.

$M_n$(calc.)=564.59 g/mol

The obtained macromere was dissolved in TGDMA as summarized in Table 1:

| Batch | | CBI 02-28-3 |
|---|---|---|
| Concentration TGDMA | % | 30 |
| Viscosity | Pas | 11.7 |
| Refractive index | — | 1.5209 |
| Flexural strength | MPa | 102 |
| E-Modulus | MPa | — |

Example 5 (CSH 01-134-1)

4.00 g (0.018 mol) resorcinol diglycidyl ether, 3.60 g (0.009 mol) butane-1,2,3,4-tetracarbonic acid di-2-hyrdoxy ethyl methacrylate (TCB-resin), 1.55 g (0.018 mol) methacrylic acid, 0.150 g triethylbenzyl ammoniumchloride and 0.003 g 2,6-di-tert-butyl-p-cresol were homogeneously mixed during heating to 90° C. and reacted for 4 hours at 90° C.

$M_n$(calc.)=1016.98 g/mol

The obtained macromere was dissolved in TGDMA as summarized in Table 1:

| Batch | | CSH01-134-2 |
|---|---|---|
| Concentration TGDMA | % | 30 |

| Batch | | CSH01-134-2 |
|---|---|---|
| Viscosity | Pas | 6.8 |
| Refractive index | — | 1.5020 |
| Flexural strength | MPa | 95.8 ± 13.1 |
| E-Modulus | MPa | 2216 ± 132 |

Application Example 1

Comparative Example 1 (AG 18-144-1)

6.808 g (0.020 mol) bisphenol-A diglycidyl ether, 1.462 g (0.010 mol) adipic acid, 1.722 g (0.020 mol) methacrylic acid, 0.091 g triethylbenzyl ammoniumchloride and 0.009 g 2,6-di-tert.-butyl-p-cresol were reacted for four hours at 90° C. The obtained methacrylate terminated macromer (n=0.5 in formula 2) is soluble in organic solvents such as chloroform, DMF and THF. In the IR-spectrum no absorption of epoxide groups at 915 and 3050 cm$^{-1}$ was observed. A new absorption of ester groups was found at 1720 cm$^{-1}$.

$M_n$ (calc.)=783.9 g/mol, η=27050 Pa*s

The obtained macromere was dissolved in TGDMA as summarized in Table 1:

| Batch | | AG 18-147-1 |
|---|---|---|
| Concentration TGDMA | % | 30 |
| Viscosity | Pas | 16.5 ± 0.14 |
| Refractive index | — | 1.5248 |
| Flexural strength | MPa | 93.3 ± 2.0 |
| E-Modulus | MPa | 2016 ± 74 |

The flexural strength and refractive index of the obtained BPA-basing macromere (n=1) are corresponding to the specified level.

Comparative Example 2 (JUM 1-46-1)

200.000 g (0.900 mol) resorcinol diglycidyl ether, 53.136 g (0.450 mol) succinic acid, 77.475 (0.900 mol) methacrylic acid, 1.653 g triethylbenzyl ammoniumchloride and 0.331 g 2,6-di-tert-butyl-p-cresol were homogeneously mixed during heating to 90° C. and reacted for 6 hours at 90° C. The obtained methacrylate terminated macromer (n=1) is soluble in organic solvents such as chloroform, DMF and THF. In the IR-spectrum no absorption of epoxide groups at 915 and 3050 cm$^{-1}$ was observed. A new absorption of ester groups was found at 1720 cm$^{-1}$.

$M_n$ (calc.)=734.8 g/mol, ]=7760 Pa*s, $n_D^{2D}$=1.5350

Comparative Example 3 (CBI 02-40-01)

10.000 g (0.036 mol) 1,2-diglycidyl phtalate, 2.122 g (0.018 mol) succinic acid, 3.094 g (0.036 mol) methacrylic acid, 0.334 g triethylbenzyl ammoniumchloride and 0.069 g 2,6-di-tert.-butyl-p-cresol were reacted for six hours at 90° C. The obtained methacrylate terminated macromer (n=1) is soluble in organic solvents such as chloroform, DMF and THF. In the IR-spectrum no absorption of epoxide groups at 915 and 3050 cm$^{-1}$ was observed. A new absorption of ester groups was found at 1720 cm$^{-1}$.

$M_n$ (calc.)=846.8 g/mol, η=2286 Pa*s, $n_D^{2D}$=1.5210

The obtained macromere was dissolved in TGDMA as summarized in Table 1:

| Batch | | CBI 2-40-2 |
|---|---|---|
| Concentration TGDMA | % | 30 |
| Viscosity | Pas | 4.56 |
| Refractive index | — | 1.4989 |
| Flexural strength | MPa | 19.07 ± 1.34 |
| E-Modulus | MPa | 219 ± 27 |

The flexural strength and refractive index of the obtained BPA-free macromere (n=1) are to low.

The invention claimed is:

1. Dental composite comprising
   (i) a polymerizable composition obtainable by reacting a mixture comprising:
      (a) x equivalents of one or more compounds of the following formula (I):

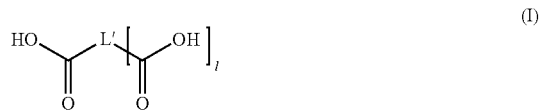

(I)

wherein
   L' is an (l+1)-valent hydrocarbon group which may contain in its backbone 1 to 3 heteroatoms selected from oxygen atoms and sulfur atoms and which may be substituted by one or more hydroxyl groups or groups COOL" wherein L" is a polymerizable moiety;
   l is an integer of from 1 to 3;
   (b) y equivalents of one or more compounds of the following formula (IIa), (IIb) and/or (IIc):

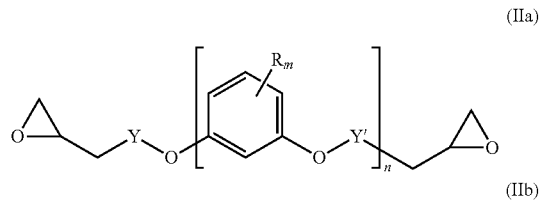

(IIa)

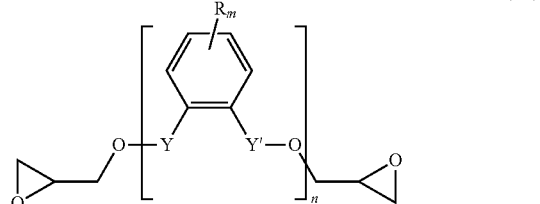

(IIb)

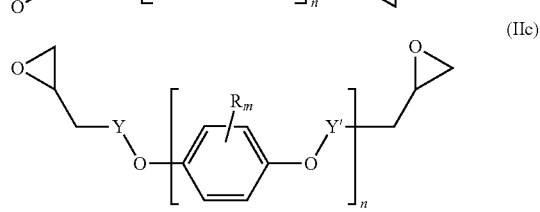

(IIc)

wherein
   n is an integer of from 1 to 3,
   Y may be present or absent, and when present represents a carbonyl group;
   Y' independently may be present or absent, represents a carbonyl group;

$R_m$ which may be the same or different represent 1 to 3 substituents selected from halogen atoms, alkyl groups, and alkoxy groups, or wherein two $R_m$ form together with the carbon atoms of the ring to which they are bonded an annelated aromatic ring; and (c) z equivalents of one or more compounds of the following formula (III):

$$\left[ R^1 \underset{O}{\overset{CH_2}{\diagdown}} O \right]_k L - X \quad (III)$$

wherein
$R^1$ is a hydrogen atom or an alkyl group;
k is an integer of from 1 to 3, whereby
when k is 1, 2 or 3, then L is a (k+1)-valent hydrocarbon group which may contain 1 to 3 heteroatoms selected from oxygen atoms and sulfur atoms, and X is a carboxylic acid group, or a hydroxyl group bonded to an aromatic ring forming part of L; or wherein $0.05 \leq x/y \leq 0.66$, and $2y - \bar{f}x \leq z \leq 1.5(2y - \bar{f}x)$, wherein x, y, and z are the molar equivalents of components (a), (b) and (c) and $\bar{f}$ is the mean acid functionality of component (a):

$$\bar{f} = \sum_{l=1}^{3} \frac{x_l}{x}(l+1)$$

wherein l is as defined in formula (I); and
optionally reacting the hydroxyl groups and/or carboxylic acid groups on L' of the reaction product of the mixture with a compound having a polymerizable double bond; and
(ii) a particulate filler.

2. The dental composite according to claim 1, wherein the mixture contains a compound of formula (IIa).

3. The dental composite according to claim 1, wherein n is 1.

4. The dental composite according to claim 1, wherein in the compound of the formula (III), wherein k is 1, L represents a single bond and X is a hydrogen atom.

5. The dental composite according to claim 1, wherein the compound of the formula (III), l is 1.

6. The dental composite according to claim 1, wherein the polymerizable composition is obtainable by reacting the hydroxyl groups on L' of the reaction product of the mixture with a compound having a polymerizable double bond.

7. The dental composite according to claim 6, wherein the compound having a polymerizable double bond is a hydroxyalkyl (meth)acrylate.

8. The dental composite according to claim 1, wherein the polymerizable composition (i) has a dynamic viscosity at 23° C. of from 1 to 30 Pas.

9. The dental composite according to claim 1, wherein the polymerizable composition (i) has a refractive index of from 1.500 to 1.540.

10. The dental composite according to claim 1, wherein the dental composite does not contain a diluent selected from organic solvents.

11. A process for the preparation of a polymerizable composition for use in a dental composite, which comprises reacting a mixture comprising:

(a) x equivalents of one or more compounds of the following formula (I):

$$HO \underset{O}{\overset{}{\diagdown}} \left[ L' \underset{O}{\overset{}{\diagdown}} OH \right]_l \quad (I)$$

wherein
L' is an (l+1)-valent hydrocarbon group which may contain in its backbone 1 to 3 heteroatoms selected from oxygen atoms and sulfur atoms and which may be substituted by one or more hydroxyl groups or groups —COOL" wherein L" is a polymerizable moiety;
l is an integer of from 1 to 3;

(b) y equivalents of one or more compounds of the following formula (IIa), (IIb) and/or (IIc):

(IIa)

(IIb)

(IIc)

wherein
n is an integer of from 1 to 3,
Y may be present or absent, and when present represents a carbonyl group;
Y' independently may be present or absent, represents a carbonyl group;
$R_m$ which may be the same or different represent 1 to 3 substituents selected from halogen atoms, alkyl groups, and alkoxy groups, or wherein two $R_m$ form together with the carbon atoms of the ring to which they are bonded an annelated aromatic ring; and (c) z equivalents of one or more compounds of the following formula (III):

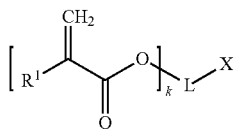
(III)

wherein
R$^1$ is a hydrogen atom or an alkyl group;
k is an integer of from 1 to 3, whereby
    when k is 1, 2 or 3, then L is a (k+1)-valent hydrocarbon group which may contain 1 to 3 heteroatoms selected from oxygen atoms and sulfur atoms, and X is a carboxylic acid group, or a hydroxyl group bonded to an aromatic ring forming part of L; or
    when k is 1, L represents a single bond and X is a hydrogen atom, wherein $0.05 \leq x/y \leq 0.66$, and $2y - \bar{f}x \leq z \leq 1.5(2y - \bar{f}x)$,
wherein x, y, and z are the molar equivalents of components (a), (b) and (c) and $\bar{f}$ is the mean acid functionality of component (a):

$$\bar{f} = \sum_{l=1}^{3} \frac{x_l}{x}(l+1)$$

wherein l is as defined in formula (I);
and optionally reacting the hydroxyl groups on L' of the reaction product of the mixture with a compound having a polymerizable double bond.

12. The process of claim 11, whereby the polymerizable composition is obtained.

13. The process according to claim 12, wherein the polymerizable composition comprises polymerizable macromers of one of the following formulae (IVa), (IVb), and/or (IVc):

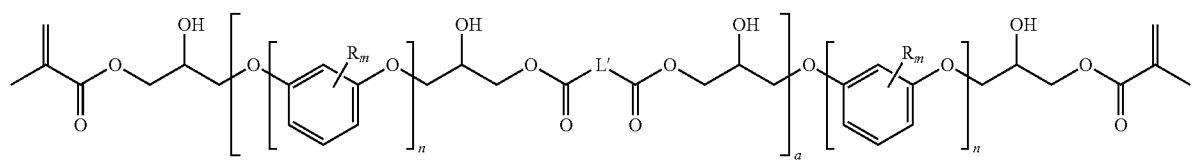
(IVa)

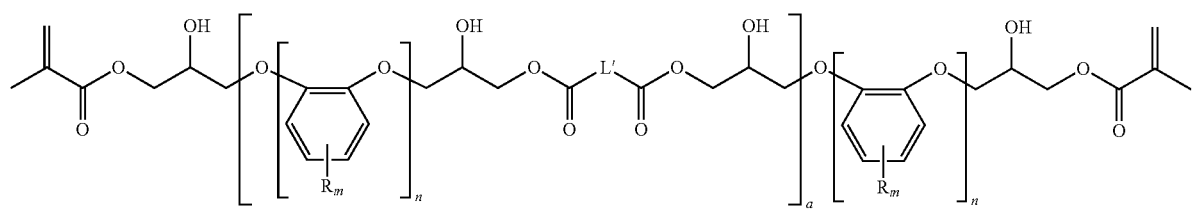
(IVb)

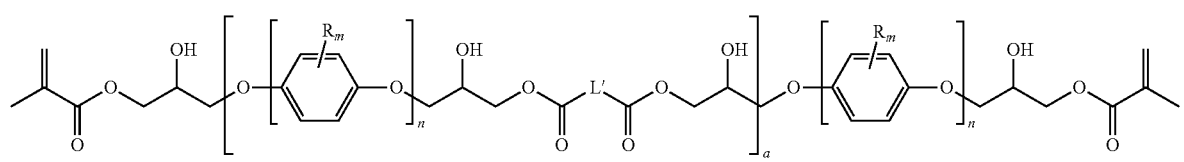
(IVc)

wherein R$^1$, R$_m$, n, and L' are as defined in claim 12, and wherein a is an average chain length which is in the range of from 0.05 to 1.5.

14. The process according to claim 13, wherein the polymerizable composition is a dental composite.

15. The process according to claim 14, wherein the dental composite is a flowable dental composite, a universal dental composite, packable dental composite or a pit and fissure sealer.

* * * * *